(12) United States Patent
Etchells et al.

(10) Patent No.: US 7,169,720 B2
(45) Date of Patent: Jan. 30, 2007

(54) MOISTURE MANAGEMENT SYSTEM (76) Inventors: Marc D. Etchells, 411 Westhampton Rd., Florence, MA (US) 01060; Joseph P. Herlihy, 119 Herrick Rd., Boxford, MA (US) 01921; Edward C. Homonoff, 66 Bush Hill Rd., Brooklyn, CT (US) 06234

( * ) Notice: Subject to any disclaimer, the term of this patent is extended or adjusted under 35 U.S.C. 154(b) by 373 days.

(21) Appl. No.: 10/680,757

(22) Filed: Oct. 7, 2003

(65) Prior Publication Data

US 2005/0075027 A1 Apr. 7, 2005

(51) Int. Cl.
 B32B 5/26 (2006.01)
 B32B 19/00 (2006.01)
 B32B 9/00 (2006.01)
 B32B 9/12 (2006.01)
 B32B 3/00 (2006.01)
 B32B 3/30 (2006.01)
 A31F 13/15 (2006.01)

(52) U.S. Cl. .................. 442/239; 442/205; 442/79; 428/357; 428/109; 428/131; 428/163; 428/172; 428/181; 428/183; 604/378; 604/384

(58) Field of Classification Search ............ 442/205, 442/239, 301, 79; 604/378, 384; 428/119, 428/357, 109, 131, 163, 171, 172, 181, 183, 428/190
See application file for complete search history.

(56) References Cited

U.S. PATENT DOCUMENTS

| | | |
|---|---|---|
| 2,869,253 A | 1/1959 | Sachs |
| 3,627,567 A | 12/1971 | Tensho |
| 4,430,811 A | 2/1984 | Okada |
| 4,465,730 A | 8/1984 | Okada |
| 4,530,873 A | 7/1985 | Okada |
| 4,645,698 A | 2/1987 | Matsubara |
| 5,141,794 A | 8/1992 | Arroyo |
| 5,217,782 A | 6/1993 | Moretz et al. |
| 5,290,269 A * | 3/1994 | Heiman ............ 604/378 |
| 5,291,617 A | 3/1994 | Moretz et al. |
| 5,306,536 A | 4/1994 | Moretz et al. |
| 5,331,059 A * | 7/1994 | Engelhardt et al. ........ 525/340 |
| 5,364,678 A | 11/1994 | Lumb et al. |
| 5,365,677 A | 11/1994 | Dalhgren |
| 5,378,529 A | 1/1995 | Bourdeau |
| 5,511,323 A | 4/1996 | Dahlgren |
| 5,614,302 A | 3/1997 | Nance, Jr. |
| 5,693,707 A | 12/1997 | Cheng et al. |
| 5,738,937 A | 4/1998 | Baychar |
| 5,746,013 A | 5/1998 | Fay, Sr. |

(Continued)

FOREIGN PATENT DOCUMENTS

WO 00/61642 10/2000

*Primary Examiner*—Terrel Morris
*Assistant Examiner*—Lynda Salvatore
(74) *Attorney, Agent, or Firm*—Wall Marjama & Bilinski LLP (57) ABSTRACT

A three dimensional fabric suitable for use as a moisture management system for footwear and apparel which includes a first surface and a second surface which encase a center section. At least one surface is water repellent and may include pores of a predetermined size to allow moisture to pass therethrough. The fabric further contains a moisture absorbing agent which functions to capture and hold moisture which is later evaporated within a predetermined time period.

45 Claims, 2 Drawing Sheets

U.S. PATENT DOCUMENTS

| | | |
|---|---|---|
| 5,763,335 A | 6/1998 | Hermann |
| 5,896,758 A | 4/1999 | Rock et al. |
| 6,048,810 A | 4/2000 | Baychar |
| 6,156,406 A | 12/2000 | Rock et al. |
| 6,235,659 B1 | 5/2001 | McAmish et al. |
| 6,289,841 B1 | 9/2001 | Caldwell |
| 6,380,298 B2 | 4/2002 | Flautt et al. |
| 6,395,957 B1 | 5/2002 | Chen et al. |
| 6,410,465 B1 | 6/2002 | Lim et al. |
| 6,432,504 B1 | 8/2002 | Yeh |
| 6,464,672 B1 | 10/2002 | Buckley |
| 6,476,104 B1 | 11/2002 | Nakamura et al. |
| 6,479,144 B2 | 11/2002 | Petrea et al. |
| 6,533,885 B2 | 3/2003 | Davis et al. |
| 6,558,784 B1 | 5/2003 | Norton et al. |
| 2001/0009830 A1 | 7/2001 | Baychar |
| 2001/0024716 A1 | 9/2001 | Chen et al. |
| 2001/0053643 A1 | 12/2001 | McAmish et al. |
| 2002/0025749 A1 | 2/2002 | Shimizu et al. |
| 2002/0094740 A1 | 7/2002 | Li et al. |
| 2002/0098761 A1 | 7/2002 | Nishimoto et al. |
| 2002/0103469 A1 | 8/2002 | Chen et al. |
| 2002/0107795 A1 | 8/2002 | Chen et al. |
| 2002/0119907 A1 | 8/2002 | Baker et al. |
| 2002/0128420 A1 | 9/2002 | Simpson et al. |
| 2002/0141898 A1 | 10/2002 | Carlucci et al. |
| 2002/0143305 A1 | 10/2002 | Yang et al. |
| 2002/0147435 A1 | 10/2002 | Coles et al. |
| 2002/0164474 A1 | 11/2002 | Buckley |
| 2002/0197396 A1 | 12/2002 | Haggquist |
| 2003/0026945 A1 | 2/2003 | Lasko |
| 2003/0149413 A1 | 8/2003 | Mehawej |
| 2003/0149414 A1 | 8/2003 | Mehawej |

\* cited by examiner

MOISTURE MANAGEMENT SYSTEM

BACKGROUND OF THE INVENTION

The present invention relates generally to footwear and apparel, and more specifically to a moisture management system designed to keep the foot and other body parts dry.

The control of moisture or body fluids such as perspiration in shoes has been a problem for many years. Because the foot is enclosed in a shoe, it is difficult for it to breath and evaporate moisture or perspiration that collects against the skin. Many systems have been developed to address the buildup of moisture in a shoe. These systems typically work by absorbing and transporting the moisture away from the foot towards the outside of the shoe to allow for perspiration to evaporate. In many cases, deodorizing materials are added to the shoe to help retard the creation of foul odors.

For example, U.S. Pat. No. 2,869,253 discloses a moisture absorbent and self-ventilating footwear article that is produced from fabrics layered and combined with compressed layers of the interior fibrous structure of the luffa plant that can be molded into shapes. One problem with this product is that the shoes made from these materials are initially stiff to the wearer and require time and walking to become more comfortable to wear.

U.S. Pat. No. 3,627,567 describes a leather-like material and process to produce it that claims having air and moisture permeability, moisture absorptivity, and moisture exhalability equivalent or better than leather. The product claims the ability to move moisture away from the foot in the shoe by strong capillary action but has the problem of rewetting the foot if the shoe does not immediately evaporate all of the liquid, leaving the feeling of a wet foot.

U.S. Pat. No. 4,430,811 presents a multilayered composite structure that is designed to absorb and transport moisture away from the wearer's foot but has the disadvantage of holding much of the moisture in capillaries in the shoe fabric. This allows the fabric to release liquid water when pressure is applied so that it can rewet the foot. A number of other patents disclose similar attempts to move liquid water or perspiration away from the foot through multilayered or interknitted constructions. These references include U.S. Pat. Nos. 4,465,730, 5,217,782, 5,291,617, 5,306,536, 5,365,677, 5,378,529, 5,614,302, 5,746,013, 6,432,504 and U.S. Patent Application Ser. Nos. US2001/0009830 and US2002/0094740.

A number of patents disclose the addition of adsorptive fillers that enhance the ability of a fabric to capture moisture or body fluid and then to hold and gel the fluid to keep it from moving about in the fabric. U.S. Pat. No. 5,763,335 describes a layered composite fabric comprised of multiple layers of fabric and a foam layer made more hydrophilic with the addition of powdered superabsorbent polymer and resistant to odor by the addition of antimicrobial agents directly into the foam as it is produced. This product has the disadvantage of being very heavy, heat-insulative, and expensive to produce for footwear. U.S. Patent Application No. US2002/0128420 describes another foam material that has added into the precurser materials small amounts of powdered absorbent fillers to enhance its moisture management properties but which also has the disadvantages of heavy weight, heat-insulation, and high cost.

U.S. Patent Application No. US2002/0025749 describes a moisture absorptive and dischargeable cloth that comprises a hydrophobic synthetic fiber portion of not less than 60 weight % with moisture highly absorptive and dischargeable organic fine particles that are bonded to the surface of the fiber by graft polymerization. U.S. Pat. No. 5,141,794 describes a multilayered structure including an impervious liquid layer that includes as one of the layers a relatively porous substrate that has been impregnated with a superabsorbent material. The material swells and gel-blocks to prevent liquid pass-through of the product.

U.S. Patent Application No. US2002014898 discloses a method of odor and liquid containment in a disposable absorbent sheet structure. The sheet is heavily treated with odor controlling agents in the absorbent structure. The product is a replaceable shoe insert and as such is not suitable as a permanent component of a shoe upper.

U.S. Pat. No. 4,530,873 discloses a sweat-absorbent textile fabric that comprises a first fabric layer that has high water permeability and low moisture absorption and a second fabric layer that has high moisture absorption substantially higher than the first fabric layer with the two layers being integrally connected together to form a double layered structure. The first fabric layer is constructed of hydrophobic polymer fibers while the second fabric layer comprises hydrophilic polymer fibers with high water retentivity. The fabric layers are constructed in a manner such that the outer water permeable layer is coarser in construction than the inner water absorptive layer. This fabric construction has the disadvantages of not functioning with a mesh appearance for style needs in many applications and allowing water not absorbed by the water absorbent layer to move through capillary action back into the water permeable fabric layer to rewet it.

U.S. Patent Application Nos. US 2002/01074945, US2002/0103469 and U.S. Pat. No. 6,395,957 disclose an absorbent web that has a dry feel produced from papermaking fibers. The absorbent web has hydrophobic matter deposited preferentially on elevated regions of the upper surface of the base sheet in a discontiguous manner. This fabric has the disadvantage of not having the strength characteristics to be suitable for use as a permanent component of footwear.

In view of the above, it can therefore be seen that there is a need for a moisture management system which addresses the shortcomings of the prior art.

SUMMARY OF THE INVENTION

It is therefore an object of the present invention to provide a moisture management system which overcomes the prior art problems described above.

It is another object of this invention to provide a moisture management system for fabrics used in footwear and apparel that keeps the user comfortable when perspiration is generated.

It is also an object of this invention to provide a system which functions to capture and accumulate moisture away from the skin of the foot and to allow it to evaporate efficiently from footwear over a short period of time.

It is yet another object of this invention to provide a system which functions to reduce the ability of odor to be created in the shoe after being worn.

The above objectives and others are accomplished by treating a knit or woven spacer fabric with a moisture management system comprised of a water repellent treatment and a water absorbent treatment. An antimicrobial agent may optionally be included in the water repellent and/or water absorbent treatment as will be described hereinafter in greater detail. The moisture management system and the process is preferably applied to a shoe spacer fabric that will move moisture or bodily fluids such as perspiration away from the wearer's foot, adsorb the moisture or perspiration and lock it in place in the spacer fabric so that it can not rewet the wearer's foot, and evaporate the moisture or perspiration, all while keeping the foot essentially dry, and further includes means for overcoming odors from bacteria and fungus caused by these fluids during their generation and adsorption in the spacer fabric. More specifically, the moisture management system is designed to keep the foot dry by directing moisture through holes in the mesh of the spacer fabric to the absorbent treatment in a portion of the fabric away from the foot that captures the moisture and locks it in place by gelling, and then allows the captured moisture to evaporate in a short period of time, such as overnight. The foot stays dry because the mesh surface against the foot has an antimicrobialwater repellent treatment applied to it that allows the perspiration to enter through the mesh holes into the interstices of the fabric for absorption and gelling, locking the moisture in place so that it cannot rewet the surface that it came from, while repelling any moisture that may try to wick back into the mesh fabric layer. The gel then allows the captured moisture to evaporate in a short period of time.

The moisture management system is typically applied to the fabric in at least two applications in series, but may also be applied in a one pass application. The repellent treatment must be applied first if the absorbent treatment will reside in the spacer fabric core. The repellent treatment is applied to the mesh side so that the fabric surface surrounding the mesh repels water-based fluids. The repellent treatment repels the application of the water-based absorbent treatment so that the absorbent treatment is forced into the center of the spacer fabric which contains a plurality of vertical fibers. When the water absorbent application has been dried, the repellent treatment will keep the repellent surface of the fabric dry to the touch. The mesh pores are large enough so that water will be forced by pressure (such as the flexing action in a shoe caused by walking) through the mesh holes. Water or moisture will migrate into the treated vertical fibers where it will be captured by the absorbent contained on the fibers to be absorbed and locked in place by gelling.

Definition Of Terms

Spacer fabric is defined as a three-dimensional woven or knitted textile fabric that typically has a first fabric layer, a second fabric layer, and yarns interconnecting the two layers, where at least a portion of the yarns interconnecting the two layers is perpendicular to each of the first and second fabric layers. The construction of the first and second fabric layers can be similar to each other or very different from each other, so that the first fabric layer can be smooth in construction and the second fabric layer can be produced with mesh holes to give it a different appearance from the first fabric layer. The spacer fabric may be constructed from polyester, nylon, acrylic, polypropylene, spandex, polylactic acid, rayon, or any combination of these fibers. Also included within this definition are composite laminated structures comprised of at least two treated fabric layers.

Absorbent is defined as a chemical component that has a capacity to absorb, gel and hold at least 10-times its dry weight of water. A wide variety of suitable materials include natural gums, starches, cellulose, carboxymethyl cellulose, alginates, pectin, gelatin and polysaccharides. Synthetic materials are also available including, polyacrylates, polyacrylimides, polyethylene oxide, acrylonitrile graft copolymers, polyvinyl alcohol and polyvinylpyrrolidines. To allow even higher capacity these materials can be latent crosslinked using reactive crosslinking agents to convert these gel-formers into water insoluble gels. The crosslinking is promoted by applying heat and/or drying, or via exposure to ultraviolet light, x-rays, beta rays, gamma rays, microwaves, steam or high humidities or organic solvent treatment. These resultant crosslinked materials are often called hydrogels or superabsorbents and are typically in a granular format but certain types can be coated on the surface of fibers, woven, knitted or nonwoven fabrics. The fluid holding capacity of a superabsorbent t is typically 15–100 times its dry weight.

Repellent is defined as the ability of a fabric to resist being wetted with liquid, typically water. A chemical component is applied to the surface of a fiber or a fabric that resists wetting by water and water-based chemicals. The repellent treatment has a surface free energy low enough that water will not be absorbed onto the surface of the treated fabric. Typical materials that act as repellent treatments include those based on fluorochemicals, oils, waxes and silicones. It is measured using a water drop test.

Water Drop Test This test determines a finished fabric's resistance to wetting by aqueous liquids. Drops of water-alcohol mixtures of varying surfaces tensions are placed on the fabric and the areas of surface wetting is determined visually. this test provides a rough index of aqueous stain resistance. Generally, the higher the water repellency testing, the better the finished fabric's resistance to staining by water-based substances. The composition of standard test liquids is shown in Table 1.

TABLE 1

| | Standard Test Liquids | | |
| --- | --- | --- | --- |
| | Composition, vol % | | Surface Tension at |
| Rating | Isopropyl Alcohol | Distilled Water | 38° C. (dry/wet) |
| 1 | 2 | 98 | 59 |
| 2 | 5 | 95 | 50 |
| 3 | 10 | 90 | 42 |
| 4 | 20 | 80 | 33 |
| 5 | 30 | 70 | 27.5 |
| 6 | 40 | 60 | 25.4 |

Procedure

1. Place fabric face up on white blotting paper on a flat horizontal surface. Beginning with test liquid No. 1, carefully place drops approximately 5 mm in diameter or 0.05 mL in volume on the test fabric in three locations.

2. Observe the drops for 10 sec from an approximate 45° angle.

3. If at least two of the three drops do not penetrate or wet the fabric and do not show wicking around the drops, place drops of test liquid No. 2 on an adjacent side, and repeat step 2.

4. Continue this procedure until at least two of the three drops have wet or show wicking into the fabric within 10 sec. The fabric's water repellency rating is the highest numbered liquid for which at least two of the three drops do not wet or wick into the fabric.

Antimicrobial is defined as the ability to slow or stop the growth of microbes including bacteria, fungus, yeast and or mold. A large number of natural and synthetic materials have bacteriostatic and/or bacteriocidal properties toward organisms normally associated with skin contact. A typical antimicrobial effectiveness screening test protocol would include the following organisms; Escherichia coli, Aspergillus niger, Candida albicans, Staphylococcus aureus and Pseudomonas aeruginosa.

There are several suitable classes of materials which can be used to deliver an effective antimicrobial property. These include certain quaternary ammonia compounds, silanes, silicone quaternary ammonium salt, surfactants, chitosan, gluteraldehyde, benzalkonium chloride, Triclosan® sold under the trademark Microbang, poly(hexamethylene biguinide) hydrochloride, iodine, and chlorine. Additionally, suitable metallic inorganic materials include silver, zinc, copper, gold, tin, lead, cadmium, palladium, bismuth, antimony, platinum and aluminum, including their metallic, nano-particle, salt, oxide, colloidal, carbonate, chloride, nitrate, sulfate, gluconate, complexed and ionic states. Many of the above can be packaged or complexed with other materials such as zeolite, ceramic and/or glass to impart slow-release properties and ease of handling. Additionally, blends of the above can be used to optimize the properties of the individual components.

Mesh is defined as a continuous fabric layer that is either woven or knitted with holes or pores of specific, controlled sizes constructed into the first fabric layer that allows for access into the spacer fabric interstices and creates a route for moisture to transfer through to the second fabric layer of the spacer fabric. A mesh may also be defined as an open fabric woven or knitted together at regular intervals, similar to a fly screen mesh.

Moisture holding capacity is defined as the ability of a fabric to absorb and hold it's maximum amount of moisture after being soaked in liquid for a known amount of time.

BRIEF DESCRIPTION OF THE DRAWINGS

For a further understanding of the invention, reference will be made to the following detailed description of the invention which is to be read in connection with the accompanying drawings, wherein.

DETAILED DESCRIPTION OF THE INVENTION

Combination Upper/Liner Fabric

Figure 1:
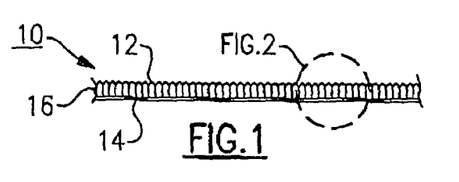
FIG. 1 is a side sectional view of one embodiment of a treated fabric which illustrates the present invention.
Figure 2:
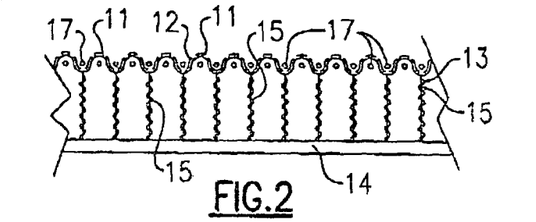
FIG. 2 is an enlarged view of FIG. 1 at the location shown in FIG. 1.

The upper liner fabric is illustrated more specifically in FIGS. 1 and 2 of the drawings. The three dimensional fabric 10 includes an upper surface 12 and a lower surface 14 and a central section 16 comprised of a plurality of vertical fibers 15. Surface 12 contains a plurality of pores 17 while lower fabric layer 14 comprises a densely knitted fabric surface without mesh holes or pores. Vertical fibers 15 are coated with and contain the gel material 13 while the upper surface 12 contains a coating of a water repellent material 11.

The spacer fabric preferred is a "double needle-bar" tricot knit three-dimensional fabric. It has a mesh first fabric layer side (outside surface of the shoe) with pores of a controlled size constructed into the outside surface, a section of vertical fibers in the center that interconnect the outer first mesh fabric layer to the inside fabric layer, and a second fabric layer inside the shoe that contacts the foot, this layer comprising a densely knitted fabric surface without mesh holes or large pores. This spacer fabric is used as the upper and lining of the outside of a shoe, usually an athletic shoe, and is usually at least about 5 yarns thick. The yarns can be individual fibers also but in most cases are true yarns (either spun or filament). One example of a spacer fabric suitable for use in this invention is 3D Air Blando Mesh, a 100% polyester spacer fabric produced by and available from Daewoo International Corporation of Seoul, South Korea.

A multiple phase moisture management system is applied to the spacer fabric. It is applied to the fabric from two separate chemical baths. The outside mesh surface has a first water-based repellent treatment with antimicrobial capability applied to the first mesh layer to impart water repellency to the outside surface. This treatment is applied by kiss-coat in a normal textile pad process that coats the outside surface of the mesh. Other textile finishing processes that can be used to apply the repellent treatment include spray, knife over roll coating, foam coat, and printing, among others. Typical application levels of repellent treatment applied to the mesh layer of the spacer fabric are between about 0.1% and 2% dry weight of the fabric, with a preferred level of about 0.1–0.5% dry weight of the fabric. The repellent treatment level will be different for each fabric and will vary with the size of the pores in the mesh. The repellent is cured in place by passing the treated fabric through an air impingement oven and exposing it to heat so that the repellent treatment reaches its cure temperature. Other energy application methods suitable for curing the repellent treatment onto the spacer fabric include contact dryer cans, through-air ovens, infrared ovens, ultraviolet light, microwave ovens, electron beam radiation, radio frequency radiation, and combinations thereof.

The size and dimensions of the mesh holes or pores are important to the design and application of this invention. If the repellent treatment is applied to a fabric without mesh pores in the fabric layer or with small mesh pores, the water will stay on the side of the fabric that it was generated on and will not be able to penetrate through this layer into the fabric so that it can become gelled by the absorbent layer. The pores or holes created in the mesh construction must be large enough to allow liquid water to be mechanically forced through them into the center of the fabric but will not allow water droplets to penetrate through the fabric easily without some external pressure being applied to the liquid water. It has been found that mesh pore sizes of between about 0.3 mm and 5.0 mm, and preferably between about 1.0 mm and 3.0 mm, are optimum for both repelling water and allowing it to transfer through the outer layer pores into the interstices of the spacer fabric.

Typical repellent treatments include water-based fluorochemicals, silicones, and waxes. An example of a fluorochemical suitable for this application is Barpel 1700 produced by Apollo Chemical Company of Burlington, NC. An antimicrobial treatment suitable for this application is AlphaSan 7000 silver-based antimicrobial powder marketed by Milliken Chemical of Spartanburg, S.C.

A second water-based moisture-absorbing antimicrobial treatment is then applied through the mesh fabric layer treated with the antimicrobial repellent treatment. This moisture absorbing treatment coats the vertical fibers in the center of the fabric and becomes an insoluble hydrogel or superabsorbent upon curing or crosslinking so that it will gel and hold liquid moisture upon insult with moisture. Curing or crosslinking can be accomplished via any method as described above. The moisture absorbing treatment is controlled so that it does not pass completely through to the smooth knit second fabric layer where it would contact the sock or skin of the foot in a shoe. The moisture absorbing treatment will absorb water and convert it into a gel which will function to mechanically lock the liquid in place in the center of the fabric. Also, it has surprisingly been found that the moisture absorbing treatment will continue to pull and absorb any liquid water in contact with it into the vertical fibers, effectively pulling any existing liquid water out of the repellent treatment first mesh layer and quickly making this layer dry to the touch.

The spacer fabric, due to it construction, has inherent high air permeability. This allows large volumes of air to pass through the fabric and over the gelled water absorbed by the water absorbent treatment. The airflow allows the water to be evaporated out of the fabric relatively quickly. The fabric dries after being left out overnight, similar to removing a shoe and setting it in the corner to wear again the next day.

The absorbent treatment is mixed from a number of components combined together in a liquid mixing container. The absorbent treatment comprises an aqueous solution polymerization polymer containing carboxylic acid that is cross-linked in situ when applied to the fabric upon drying by addition of a crosslinking chemical. Examples of this system and suitable components to produce it are disclosed in PCT Application No. WO 00/61642 (Anderson et al) and U.S. Pat. No. 5,963,707 (Cheng et al) and U.S. Pat. No. 4,090,013 which are incorporated herein by reference. An example of the aqueous solution polymerization polymer suitable for this application is FULATEX PD-8081-H produced by H.B. Fuller Company in Vadnais Heights, Minn. Examples of suitable crosslinking agents include Bacote 20 ammonium zirconium carbonate produced by Magnezium Elektron, Inc. of Flemington, N.J. and Neocryl CX-100 aziridine crosslinking agent from Neoresins, Inc. of Wilmington, Mass.

Humectants are added to the mix to attract moisture from the atmosphere to partially hydrolyze and soften the fiber/fabric absorbent treatment. Suitable humectants include glycerin (glycerol), propylene glycol (PEG), ethylene glycol, mineral oil, lanolin, sorbitol, maltitol, and sodium PCA. Glycerin is a preferred humectant and can be purchased from Cognis Corp., Cincinnati Ohio. Polyethylene glycol is also preferred and can be purchased from Dow Chemical, Houston, Tex. under the trade name of Carbowax.

Antimicrobial materials are added as needed to the absorbent formulation as in the repellent treatment and at similar dry weight of fabric addition levels in the final product. Typical antimicrobial absorbent treatment add-on levels to the spacer fabric in this embodiment of the invention are between about 0.1% and 10% dry weight of product, and preferably between about 0.5% and 5% dry weight of fabric, and are different for each construction of spacer fabric selected.

The repellent treated spacer fabric is run through a textile pad unit where the absorbent treatment is applied through the repellent mesh fabric layer side and forced into the center of the spacer fabric through the mesh holes of the first repellent treated layer by a roll nip. Application methods of the moisture-absorbing treatment to the spacer fabric are similar to the repellent treatment but kiss and nip through the repellent treated mesh layer is preferred in this invention embodiment. The fabric is then dried so that the absorbent treatment crosslinks in situ to form an antimicrobial/moisture absorbent coating on the vertical fibers. The resultant moisture management treated fabric is then collected on a winder and prepared for shipping.

The repellent treatment can also be applied by alternative methods. To do this, the yarns or filaments of the fabric can be pre-treated with the repellency chemistry prior to knitting. The chemical application is accomplished by passing the yarns or filaments through a bath or pad roll or kiss roll applicator, via spraying or via co-extrusion of the core polymer filament with a sheath component containing the repellent chemistry. The construction of the spacer fabric can be chosen and designed such that these repellent yarns or filaments are placed in an appropriate position within the fabric structure such that they function to act as a repellent layer. Textile designers are well versed in the techniques of positioning multiple yarns or filaments in various positions within the structure.

The absorbent treatment can also be applied via alternative methods. To do this, the yarns or filaments can be pre-treated with the absorbent chemistry prior to knitting. The chemical application is accomplished by passing the yarns or filaments through a bath or pad roll or kiss roll applicator, via spraying or via co-extrusion of the core polymer filament with a sheath component containing the absorbent chemistry. The construction of the spacer fabric can be chosen and designed such that these absorbent yarns or filaments are placed in an appropriate position within the fabric structure such that they function to act as a moisture reservoir.

It is also possible to impart both repellent and absorbent features by pre-treating the respective yarns or filaments prior to knitting as described above.

The following example illustrates one method of making the upper/liner fabric described above.

EXAMPLE I

Antimicrobial water repellent and antimicrobial water absorbent treatments are applied to an Air Blando Mesh 100% polyester double-needle bar knit fabric by the following technique. The fabric mesh pores were measured as:

length—2.8 mm width—1.6 mm

The repellent mix was prepared using the following formulation:

7600 grams water 400 grams Barpel 1700

1.2 grams AlphaSan RC7000

This mix is added to a standard textile pad unit with one roll partially submerged in the mix and a squeeze roll on top of the submerged roll. On top of the squeeze roll a free-turning rider roll is positioned which functions to press the fabric against the squeeze roll to enhance wet pickup of the mix when the mesh side of the fabric is being kiss-coated with chemistry. The fabric is kiss-coated at 9.4 ft/min line speed and run into an air impingement oven to dry and cure the repellent mix at 300° F. web surface temperature. The calculated web dry solids pickup of the repellent mix is about 0.25% by dry weight of fabric.

The repellent treated mesh side of the fabric is measured for repellency rating using the Water Drop Test (reference attached) and has a rating of between about 3 and 4.

The absorbent treatment is then applied through the repellent treated mesh side of the fabric. The mix is prepared using the following formulation:

15000 grams water
750 grams Fulatex PD-8081-H
97.5 grams Carbowax Sentry 600
37.5 grams AlphaSan RC7000
79.2 grams Bacote 20

The fabric is run through the closed nip between the submerged roll and the squeeze roll with the repellent treated mesh side against the submerged roll. Calculated dry solids pickup for the absorbent treatment is about 0.39% dry weight of fabric. Line speeds and oven temperatures are the same as described above. The final repellent/absorbent treated fabric has a moisture holding capacity of about 102% dry weight of fabric with a repellency rating of between about 3 and 4.

Liner Fabric In a second embodiment of the invention, a liner fabric is designed to hold large amounts of moisture away from the foot. It may use the same spacer fabric as the upper/liner fabric described above but has the water-absorbing treatment applied to the second smooth layer surface so that the water can become gelled and captured as far from the foot as possible.

Figure 3:
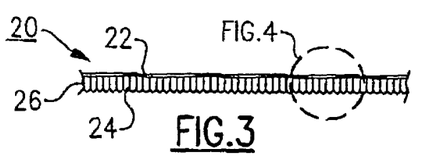
FIG. 3 is a side sectional view of a second embodiment of a treated fabric which illustrates the present invention.
Figure 4:
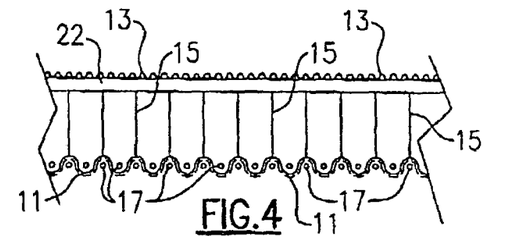
FIG. 4 is an enlarged view of FIG. 3 at the located shown in FIG. 3.

The liner fabric is more specifically illustrated in FIGS. 3 and 4 of the drawings. In this embodiment the liner fabric 20 comprises an upper fabric layer 22 and lower fabric layer 24, and a central core section 26 made up of vertical fibers 15. The lower fabric layer 24 contains a mesh or pores 17 and is treated with an outer water repellent layer 11, while close knit fabric layer 22 is treated with an outer coating or layer of the gel material 13.

In this embodiment of the invention, the antimicrobial repellent treated mesh first layer of the spacer fabric resides against the foot, and the smooth knit second layer is positioned away from the foot, opposite the fabric direction in the first embodiment described above. The mesh first layer has a water-based repellent antimicrobial treatment applied to it in the same manner and at a similar dry weight addition as in Example I above. This treatment helps keep the foot dry when liquid perspiration has been forced into and through the mesh layer.

The second moisture absorbing antimicrobial treatment is preferably kiss-coated and dried onto the smooth second layer of the spacer fabric. Acceptable application methods for both treatments in this embodiment are similar to those described for the upper/liner fabric embodiment. The moisture-absorbing treatment application can be a second pass operation but can also be applied as a single pass operation at the same time as the repellent treatment is applied so that both the repellent and absorbent treatments are applied to the spacer fabric and dried in a single textile finishing pass. In this embodiment, there is no moisture absorbing treatment applied to the vertical fiber section of the fabric. The purpose of treating the side away from the foot with the moisture absorbing antimicrobial treatment is to gel and lock in place away from the foot the liquid perspiration generated when wearing the shoe. This product may have significantly more moisture holding capability than the upper/liner fabric if this feature is necessary in the product. The absorbent treatment mix used for this embodiment is similar to that described above. The dry solids add-on levels may be much higher than those needed in the previous embodiment of the invention. For example, depending on the final product properties desired and the spacer fabric selected, suitable dry weight additions can range from about 0.1% to 5% dry weight of fabric, and preferably ranging between about 0.2% and 2% dry weight of fabric.

The following example illustrates one method of making the liner fabric described above.

EXAMPLE II

The same mesh spacer fabric is used as in the upper/liner fabric of Example I. The repellent mix, process application, and oven speed and temperature are determined as in the upper/liner fabric example. The resultant repellent treatment solids add-on are about 0.13% dry weight of fabric. The treated repellent fabric has repellency ratings of between about 3 and 4.

The absorbent mix is prepared using the following formulation:

15000 grams water
1500 grams Fulatex PD-8081-H
200 grams Carbowax Sentry 600
37.5 grams AlphaSan RC7000
75.0 grams Aerosol OT-75
78.9 grams Bacote 20

The absorbent treatment is kiss-coated onto the smooth side of the fabric using the same kiss-coat speed and oven temperature settings as described in the upper/liner fabric example. The absorbent treatment solids add-on is about 0.66% dry weight of fabric. The resultant product has repellency test ratings of between about 3 and 4 and moisture holding capacity of about 191% dry weight of fabric.

Double-sided Mesh A third embodiment of the invention is based on a spacer fabric that has a mesh fabric layer surface for both the top and bottom surfaces. It is called a "double-sided" mesh spacer fabric. A suitable fabric is 3D Open Blando Mesh III spacer fabric manufactured by Daewoo International of Seoul, Korea.

Figure 5:
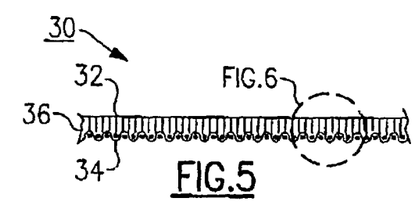
FIG. 5 is a side sectional view of a third embodiment of a treated fabric which illustrates the present invention.
Figure 6:
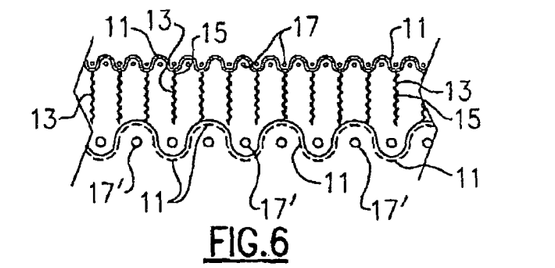
FIG. 6 is an enlarged view of FIG. 5 at the located shown in FIG. 5.

The double side mesh embodiment is illustrated more specifically in FIGS. 5 and 6 of the drawings. In this embodiment both top layer 32 and bottom layer 34 each contain mesh, and a central core section 36 made up of vertical fibers 15. Layer 32 contains mesh 17 while layer 34 contains a relatively larger mesh 17'. Both layers 32 and 34 also contain a water repellent coating 11, with vertical fibers 15 containing the gel component 13.

In this embodiment, fabric layer 34 is typically constructed of larger pores than layer 32. In use, the mesh fabric layer side with larger pores resides on the skin side of the shoe while the smaller mesh pore side is on the outside of the shoe. Both mesh surfaces are treated with the water-based repellent antimicrobial treatment at the levels described in Examples I and II. The outside surface with the smaller mesh is somewhat more repellent than the inside surface against the foot due to the smaller size of the mesh pores requiring more pressure to force liquid moisture through the fabric into the fabric interstices. The moisture absorbing antimicrobial treatment is applied through one of the treated mesh fabric layer surfaces into the center vertical fiber section of the fabric. Absorbent treatment mix compositions, dry solids addition levels, and textile finish application methods are similar to those described in the upper/liner fabric embodiment. The moisture management system works in the same manner as in the upper/liner fabric previously described. The repellent mesh on the outside of the fabric functions to keep water from penetrating into the fabric from the outside environment. The repellent mesh surface against the skin will allow liquid perspiration to penetrate through the mesh pores into the absorbent center vertical fiber section of the fabric where the liquid is gelled and held mechanically in place to be later evaporated from the absorbent treatment. The open mesh allows air to pass through the fabric unimpeded and enhances evaporation of the liquid from the gel into the atmosphere. The surface against the foot stays dry as the liquid is attracted and absorbed into the absorbent layer.

The following example illustrates one method of making the double sided mesh fabric described above.

EXAMPLE III

A fabric having mesh pores on both sides of the material sold under the tradename 3D Open Blando Mesh III 100% polyester double needle bar knit, by Daewoo International Corporation of Korea is used in this embodiment. The pores are larger on one side than the other. While both mesh sides are kiss-coat repellent treated, the smaller pore side is selected to be on the outside of the shoe. The pore dimensions are:

Large pore side:
   length—2.0 mm
   width—1.6 mm
Small pore side:
   length—1.8 mm
   width—1.2 mm The repellency mix and process setup are the same as described in the upper/liner fabric Example 1. Repellent treatment dry solids application is measured at 0.13% dry weight of fabric. Repellency ratings of between 3 and 4 are obtained from the resultant treated fabric.

The absorbent treatment mix and process of application are the same as those described in Example 1. The fabric has 0.2% dry solids pickup in the product. The final product exhibits 75% moisture holding capacity with repellency ratings of between 3 and 4 on each side of the final product.

Variable Profile fabric In a further embodiment, the fabric has a variable height profile on one side with the appearance of hills, nubs or ridges in the fabric surface face and an opposite second smooth surface on the other fabric face.

Figure 7:
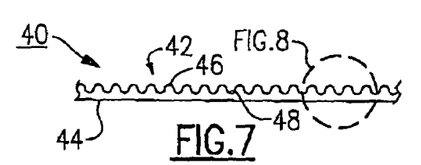
FIG. 7 is a side sectional view of a fourth embodiment of a treated fabric which illustrates the present invention.
Figure 8:
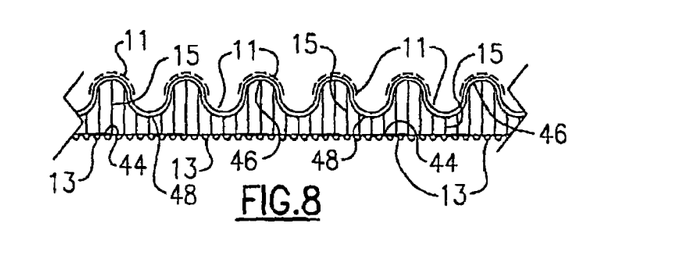
FIG. 8 is an enlarged view of FIG. 7 at the located shown in FIG. 7.

The variable profile fabric is illustrated more specifically in FIGS. 7 and 8 of the drawings. The variable profile fabric 40 consists of an upper surface 42 which is made up of a series of nubs which create hills 46 and valleys 48 with a second smooth bottom surface 44 supporting the nubbed upper surface. The hills 46 are coated with a water repellent material 11 while the bottom smooth fabric surface contains a coating of gel component 13.

The following example illustrates another embodiment of the invention.

EXAMPLE IV

In this example, the nubbed surface creates hills of fabric with valleys of air between them that allows for increased airflow around and through the fabric to enhance cooling and evaporation of moisture and sweat. An example of this fabric is available under the tradename 3D Punch Back Mesh 100% polyester double needle bar knit fabric sold by Daewoo International Corporation of Korea.

The same antimicrobial repellent and absorbent mixes are used for producing the treated profile fabric as in the upper/liner fabric of Example 1. The repellent mix is applied by running the variable profile fabric first through the closed saturator nip with the variable profile side down towards the repellent mix. Line speed is set at 5 ft/min with the web temperature in the oven reading at about 300° F. The repellent dry solids pickup in the fabric results in 0.29% pickup dry weight of fabric. The tops of the nubs exhibit repellency rating values in the range of between 3 to 4.

The absorbent mix is applied as a heavy kiss-coat treatment. The saturator is set-up as in the upper/liner fabric Example 1. The absorbent mix used is the same as that described in the liner fabric embodiment. The absorbent treatment dry solids pickup in the fabric is 0.33% dry weight of fabric. The line speed is set at 16.5 ft/min and the web temperature is controlled at about 300° F. for drying purposes. The resultant fabric has repellency ratings on the tops of the nubs of between 3 to 4 and moisture holding capacity of about 105.2 grams.

Figure 9:
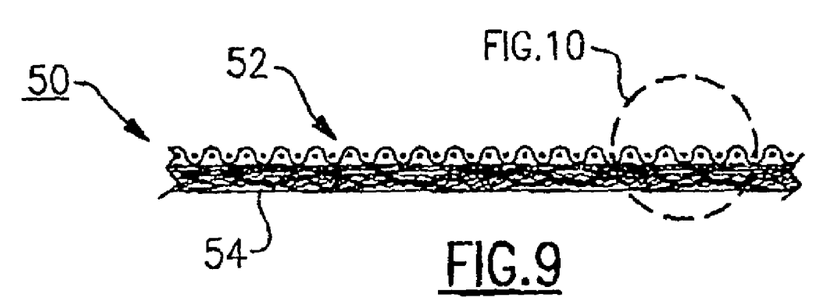
FIG. 9 is a side sectional view of a fifth embodiment of a treated fabric which illustrates the present invention.
Figure 10:
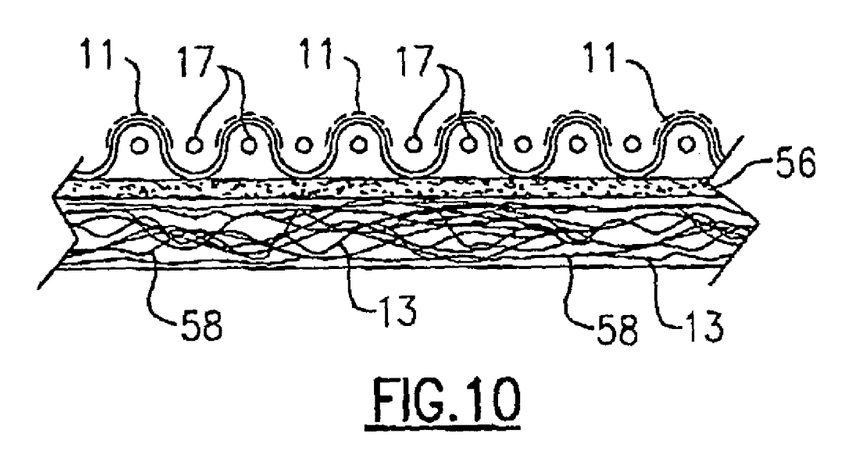
FIG. 10 is an enlarged view of FIG. 9 at the location shown in FIG. 9.

Another embodiment of the invention is illustrated in FIGS. 9 and 10 of the drawings. The fabric 50 is of a laminated configuration and includes an upper fabric layer 52 and a lower fabric layer 54 laminated together at 56. Upper fabric 52 contains a plurality of pores 17 while lower fabric layer 54 comprises a nonwoven material without mesh holes or pores. Fibers 58 in lower fabric 54 are coated with and contain the gel material 13 while the upper fabric surface 52 contains a coating of a water repellent material 11.

In this embodiment of the invention, a standard mesh fabric is treated on a first side with an antimicrobial/repellent treatment. The repellent treatment can be antimicrobial in nature as previously discussed. The treatment is coated on the fabric using the same techniques as described in the previous embodiments and then dried and cured. A 100% polyester nonwoven fabric is then treated with an antimicrobial/water absorbing treatment similar to the other embodiments. The nonwoven fabric can be a needlepunch felt or hydroentangled, spunbond, meltblown, stitchbond, airlaid, wetlaid, or drylaid material. The nonwoven fabric can be constructed from polyester, nylon, acrylic, polypropylene, polylactic acid, rayon, or any combination of these. The water absorbent treatment is applied by saturation, print/gravure coating, or other techniques described in the previous embodiments. Once applied, the treated fabric is dried. The mesh fabric untreated second face surface is laminated to the treated nonwoven. Lamination techniques include print bond adhesive, hot melt, film, split film, binder fabric, ultrasonic welding, reactive adhesives, and flame lamination processes. The resultant fabric composite has similar moisture management system functions as the liner fabric described above where the repellent treated mesh will force liquid moisture through the mesh holes and away from the repellent fabric face into the treated nonwoven away from the skin where it is gelled for later evaporation. The repellent treated mesh surface keeps moisture away from the skin of the wearer so that the skin remains dry.

Process The key to the ability of the moisture management system to have an absorbent treatment in the center of the spacer fabric is that the first repellent treatment is first applied and cured to the mesh layer of the spacer fabric so that it will repel the second absorbent treatment when it is applied through the same mesh pores, forcing it off of the surface of the fabric and into the center vertical fiber fabric section of the spacer fabric. There is a relationship between the level of repellent treatment required to force the absorbent treatment into the vertical fiber section and the concentration of absorbent solution polymer used in the absorbent treatment mix. While this is different for each mesh construction in a spacer fabric, it has been found that the best range of repellent treatment applied to the mesh first surface of the spacer fabric is at least about 0.1% dry weight of fabric. The upper limit is variable and will be defined by the fabric mesh pore construction and how easily the liquid moisture can be forced through the mesh pores.

The absorbent treatment concentration that is best combined with this level of repellent treatment in the repellent treated spacer fabric is between about 4 parts water to 1 part solution polymer, preferably between about 15 parts water to 1 part solution polymer, and most preferably between about 20 parts water and 1 part solution polymer.

While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A three dimensional fabric suitable for use as a moisture management system for footwear and apparel which comprises:
a fabric having a first surface and a second surface which encase a center section, with said first surface having a water repellent mesh surface containing a plurality of pores, said second surface being a densely constructed fabric surface having no mesh holes or pores, with said center section comprising vertical fibers which are coated with a moisture absorbing agent, whereby when said first surface and/or said second surface are contacted with liquid moisture they function to allow said liquid moisture to pass through said surface(s) into said center section where said moisture absorbing agent absorbs and captures said moisture, and later evaporates the moisture within a predetermined time period.

2. The fabric of claim 1 in which the fabric material is at least one selected from the group consisting of polyester, nylon, acrylic, polypropylene, spandex, polylactic acid, rayon and any combination thereof.

3. The fabric of claim 1 in which the repellency rating is between about 3 and 4.

4. The fabric of claim 1 in which the mesh pore size is between about 0.3 mm and 5.0 mm.

5. The fabric of claim 1 which further contains an antimicrobial agent.

6. The fabric of claim 1 in which the moisture absorbing agent is selected from the group consisting of hydrogels, superabsorbents and hydrocolloids and mixtures thereof.

7. The fabric of claim 1 in which the repellent property is imparted by the pre-treating of certain yarns or filaments of the fabric that are strategically placed within the fabric structure during its fabrication.

8. The fabric of claim 1 in which the absorbent property is imparted by the pre-treating of certain yarns or filaments of the fabric that are strategically placed within the fabric structure during its fabrication.

9. The fabric of claim 1 in which both repellent and absorbent properties are imparted by the pre-treating of certain yarns or filaments of the fabric that are strategically placed within the fabric structure during its fabrication.

10. A three dimensional fabric suitable for use as a moisture management system for footwear and apparel which comprises:
a fabric having a first surface and a second surface which encase a center section, with said first surface having a smooth surface construction which is treated with a moisture absorbing agent and said second surface having a water repellent mesh surface, with said center section comprising vertical fibers, whereby liquid moisture generated adjacent said second surface passes through said mesh into said center section to said first surface and is absorbed and captured by said moisture absorbing agent on said first surface and later evaporated within a predetermined time period.

11. The fabric of claim 10 in which the fabric material is at least one selected from the group consisting of polyester, nylon, acrylic, polypropylene, spandex, polylactic acid, rayon and any combination thereof.

12. The fabric of claim 10 in which the repellency rating is between about 3 and 4.

13. The fabric of claim 10 in which the mesh pore size is between about 0.3 mm and 5.0 mm.

14. The fabric of claim 10 which further contains an antimicrobial agent.

15. The fabric of claim 10 in which the moisture absorbing agent is selected from the group consisting of hydrogels, superabsorbents and hydrocolloids and mixtures thereof.

16. The fabric of claim 10 in which the repellent property is imparted by the pre-treating of certain yarns or filaments of the fabric that are strategically placed within the fabric structure during its fabrication.

17. The fabric of claim 10 in which the absorbent property is imparted by the pre-treating of certain yarns or filaments of the fabric that are strategically placed within the fabric structure during its fabrication.

18. The fabric of claim 10 in which both repellent and absorbent properties are imparted by the pre-treating of certain yarns or filaments of the fabric that are strategically placed within the fabric structure during its fabrication.

19. A three dimensional fabric suitable for use as a moisture management system for footwear and apparel which comprises:
a fabric having a first surface and a second surface which encase a center section, with said first surface being water repellent and having pores of a predetermined size, and said second surface being water repellent and having pores of a predetermined size, but larger than the pores of said first surface, with both of said surfaces functioning to allow moisture to pass therethrough, with said center section comprising vertical fibers which are coated with a moisture absorbing agent whereby moisture penetrating into said center section of said fabric from either of said first or second surfaces is captured and held in place by said absorbing agent and later evaporated within a predetermined time period.

20. The fabric of claim 19 in which the fabric material is at least one selected from the group consisting of polyester, nylon, acrylic, polypropylene, spandex, polylactic acid, rayon and any combination thereof.

21. The fabric of claim 19 in which the repellency rating is between about 3 and 4.

22. The fabric of claim 19 in which the mesh pore size is between about 0.3 mm and 5.0 mm.

23. The fabric of claim 19 which further contains an antimicrobial agent.

24. The fabric of claim 19 in which the moisture absorbing agent is selected from the group consisting of hydrogels, superabsorbents and hydrocolloids and mixtures thereof.

25. The fabric of claim 19 in which the repellent property is imparted by the pre-treating of certain yarns or filaments of the fabric that are strategically placed within the fabric structure during its fabrication.

26. The fabric of claim 19 in which the absorbent property is imparted by the pre-treating of certain yarns or filaments of the fabric that are strategically placed within the fabric structure during its fabrication.

27. The fabric of claim 19 in which both repellent and absorbent properties are imparted by the pre-treating of certain yarns or filaments of the fabric that are strategically placed within the fabric structure during its fabrication.

28. A three dimensional fabric suitable for use as a moisture management system for footwear and apparel which comprises:
a fabric having a first surface of a variable height profile on one side in the form of hills, ridges, or nubs with a lower area or valley therebetween and a second relatively smooth surface which supports said first surface and said first surface having a water repellent agent thereon and said second surface having a moisture absorbing agent thereon, whereby when said first surface is contacted with liquid moisture functions to allow said liquid moisture to pass through said surface to said second surface where said moisture absorbing agent absorbs and captures said moisture, and later evaporates the moisture within a predetermined time period.

29. The fabric of claim 28 in which the fabric material is at least one selected from the group consisting of polyester, nylon, acrylic, polypropylene, spandex, polylactic acid, rayon and any combination thereof.

30. The fabric of claim 28 in which the repellency rating is between about 3 and 4.

31. The fabric of claim 28 in which the mesh pore size is between about 0.3 mm and 5.0 mm.

32. The fabric of claim 28 which further contains an antimicrobial agent.

33. The fabric of claim 28 in which the moisture absorbing agent is selected from the group consisting of hydrogels, superabsorbents and hydrocolloids and mixtures thereof.

34. The fabric of claim 28 in which the repellent property is imparted by the pre-treating of certain yarns or filaments of the fabric that are strategically placed within the fabric structure during its fabrication.

35. The fabric of claim 28 in which the absorbent property is imparted by the pre-treating of certain yarns or filaments of the fabric that are strategically placed within the fabric structure during its fabrication.

36. The fabric of claim 28 in which both repellent and absorbent properties are imparted by the pre-treating of certain yarns or filaments of the fabric that are strategically placed within the fabric structure during its fabrication.

37. A three dimensional fabric suitable for use as a moisture management system for footwear and apparel which comprises:
a fabric having a first surface and a second surface which encase an inner section, with said fabric containing a water repellent on at least one surface thereof, with said water repellent surface being in the form of a mesh which contains a plurality of pores, with said fabric further containing a moisture absorbing agent, whereby liquid moisture generated adjacent at least one of said surfaces is absorbed and captured by said moisture absorbing agent and later evaporated within a predetermined time period.

38. The fabric of claim 37 in which the fabric material is at least one selected from the group consisting of polyester, nylon, acrylic, polypropylene, spandex, polylactic acid, rayon and any combination thereof.

39. The fabric of claim 37 in which the repellency rating is between about 3 and 4.

40. The fabric of claim 37 in which the mesh pore size is between about 0.3 mm and 5.0 mm.

41. The fabric of claim 37 which further contains an antimicrobial agent.

42. The fabric of claim 37 in which the moisture absorbing agent is selected from the group consisting of hydrogels, superabsorbents and hydrocolloids and mixtures thereof.

43. A three dimensional fabric suitable for use as a moisture management system for footwear and apparel which comprises:
a fabric having a first surface and a second surface which encase an inner section, with said fabric containing a water repellent on at least one surface thereof with said fabric further containing a moisture absorbing agent, and where said water repellent is imparted by the pre-treating of certain yarns or filaments of the fabric that are strategically placed within the fabric structure during its fabrication whereby liquid moisture generated adjacent at least one of said surfaces is absorbed and captured by said moisture absorbing agent and later evaporated within a predetermined time period.

44. The fabric of claim 37 in which the absorbent property is imparted by the pre-treating of certain yarns or filaments of the fabric that are strategically placed within the fabric structure during its fabrication.

45. A three dimensional fabric suitable for use as a moisture management system for footwear and apparel which comprises:
a fabric having a first surface and a second surface which encase an inner section, with said fabric containing a water repellent on at least one surface thereof with said fabric further containing a moisture absorbing agent, and where both said repellent and moisture absorbent agent are imparted by the pre-treating of certain yarns or filaments of the fabric that are strategically placed within the fabric structure during its fabrication whereby liquid moisture generated adjacent at least one of said surfaces is absorbed and captured by said moisture absorbing agent and later evaporated within a predetermined time period.

* * * * *

UNITED STATES PATENT AND TRADEMARK OFFICE
CERTIFICATE OF CORRECTION

PATENT NO. : 7,169,720 B2  Page 1 of 1
APPLICATION NO. : 10/680757
DATED : January 30, 2007
INVENTOR(S) : Marc D. Etchells, Joseph P. Herlihy and Edward C. Homonoff It is certified that error appears in the above-identified patent and that said Letters Patent is hereby corrected as shown below:

On the title page, item [56]:
On page 2, under U.S. Patent Documents. Patent document "2002/0107795" is incorrect, please replace with --2002/0107495--;

Column 2, Line 30 the patent document "US2002/01074945" is incorrect, please replace with --US2002/0107495--;

Column 3, Line 15 the word "antimicrobialwater" is incorrect, please replace with --antimicrobial/water--;

Column 4, Line 8, the phrase "superabsorbent t is typically 15-100 times" is incorrect, please replace with --superabsorbent is typically 15-100 times--;

Column 4, Line 23, the word "this" is incorrect, please replace with --This--;

Column 5, Line 6, the word "Microbang" is incorrect, please replace with --Microban$_®$--.

Signed and Sealed this

Twenty-sixth Day of February, 2008

JON W. DUDAS
*Director of the United States Patent and Trademark Office*